United States Patent [19]
Vernaleken et al.

[11] 3,960,968

[45] June 1, 1976

[54] METHOD FOR THE CONTINUOUS PRODUCTION OF AQUEOUS DIALKALI SALT SOLUTIONS OF AROMATIC DIHYDROXY COMPOUNDS

[75] Inventors: Hugo Vernaleken, Krefeld; Ludwig Bottenbruch, Krefeld-Bockum; Gerhard Emmer, Krefeld; Uwe Hucks, Duisburg, all of Germany

[73] Assignee: Bayer Aktiengesellschaft, Leverkusen, Germany

[22] Filed: June 27, 1974

[21] Appl. No.: 483,738

[30] Foreign Application Priority Data
July 13, 1973  Germany............................ 2335687

[52] U.S. Cl.......................... 260/619 R; 260/619 A; 260/620; 260/621 P; 260/625; 23/286
[51] Int. Cl.²......................................... C07C 37/00
[58] Field of Search ........ 260/619 A, 619 R, 621 P, 260/625, 620; 23/286

[56] References Cited
UNITED STATES PATENTS

| | | | |
|---|---|---|---|
| 1,878,082 | 9/1932 | Williams........................... | 260/621 P |
| 1,955,080 | 4/1934 | Mill................................. | 260/619 R |
| 2,353,725 | 7/1944 | Gump .............................. | 260/619 R |
| 2,769,833 | 11/1956 | Weil ................................ | 260/621 P |
| 3,023,252 | 2/1962 | Senior ............................. | 260/621 P |

*Primary Examiner*—Norman Morgenstern
*Attorney, Agent, or Firm*—Burgess, Dinklage & Sprung

[57] ABSTRACT

In a process for continuously producing solutions of dialkali or dialkaline earth metal salts of aromatic dihydroxy compounds, the aromatic dihydroxy compound is sprayed in the form of a melt onto a turbulent liquid film of a solution of an alkali or alkaline earth metal hydroxide. The alkali or alkaline metal hydroxide is preferably solved in water.

12 Claims, 2 Drawing Figures

METHOD FOR THE CONTINUOUS PRODUCTION OF AQUEOUS DIALKALI SALT SOLUTIONS OF AROMATIC DIHYDROXY COMPOUNDS

The present invention relates to a process for continuously producing solutions of dialkali or dialkaline earth metal salts of aromatic dihydroxy compounds.

Aqueous dialkali salt solutions of aromatic dihydroxy compunds are generally produced in batches by introducing a weighed quantity of the corresponding dihydroxy compound, preferably freed from traces of oxygen beforehand by degassing or rinsing with nitrogen, into a dilute aqueous alkali hydroxide solution.

This process is normally carried out in stirrer-equipped vessels. The residence time is governed by the size of the batch and generally amounts to between 60 and 180 minutes for batches of from 0.5 to 2 $t$ of dihydroxy compound.

It is possible in this way to produce dialkali salt solutions with a reproducible, narrow tolerance range in regard to solids concentration. Difficulties are involved in removing the traces of oxygen. Oxygen is undersirable in solutions of this kind, because it results in discolouration thereof. Discolouration attributable to the influence of oxygen is often the cause of defective colouring in polycarbonates produced from solutions of this kind.

The batch production of dialkali salt solutions is unsuitable for the production of polycarbonates on a fairly large scale. Dialkali salts can only be continuously prepared in a cascade of stirrer-equipped vessels at considerable expense. Particular difficulties are involved in continuously introducing the starting products and in degassing the solid.

The object of the invention is to provide a simple, reliable method for the continuous production of solutions of dialkali or dialkaline earth metal salts of aromatic dihydroxy compounds. According to the invention, there is provided a process for continuously producing solutions of dialkali or dialkaline earth metal salts of aromatic dihydroxy compounds, wherein an aromatic dihydroxy compound is sparyed in the form of a melt onto a turbulent liquid film of a solution of an alkali or alkaline earth metal hydroxide.

The particular advantage of the method according to the invention is that the reaction times required for dissolving the aromatic dihydroxy compounds are extremely short, amounting to less than 1 minute. Since all the component streams are introduced as liquids in the method according to the invention, dialkali salt solutions with solids and alkali concentrations in a predeterminable, narrow tolerance range are obtained. An unexpected advantage of the method according to the invention is the very good colour quality of the dialkali salt solutions and of the polycarbonates obtainable from them. The very good colour quality is surprising because aromatic dihydroxy compounds show a tendency to undergo cleavage reactions at elevated temperatures, especially in the presence of alkali.

In one embodiment of the method according to the invention, the liquid film is produced in a reactor by tangentially introducing a component stream of the aqueous alkali hydroxide solution, and spraying the molten dihydroxy compounds through nozzles.

The particular advantage of this embodiment of the method according to the invention is that it produces a uniform liquid film of the aqueous alkali hydroxide solution onto which the molten dihydroxy compound is sprayed in the form of fine particles.

In another embodiment of the method according to the invention, the melts of the dihydroxy compounds are sprayed through a nozzle system into a cylindrical reactor onto, and dissolved in, the turbulent liquid film in a defined quantity, the reactor being provided with cooling systems and the turbulent liquid film being produced by tangentially introducing a defined stream of an aqueous alkali hydroxide solution and a component stream of the reaction solution which can amount to between 0.5 and 20 times the aqueous alkali hydroxide solution introduced.

The particular advantage of this embodiment of the method according to the invention is that conversion can be controlled during the reaction, in addition to which undesirable temperature ranges are avoided.

In order to minimise thermal stressing of the reaction product, the installation is designed in such a way that, in another embodiment of the method according to the invention, the average residence time of the aqueous dialkali salt solutions of the aromatic dihydroxy compounds amounts to between about 0.5 to 20 minutes.

In another embodiment of the method according to the invention, virtually any aromatic dihydroxy compounds and mixtures thereof which, in the form of melts, are stable for at least one minute and whose alkali salts have the necessary solubility in water, can be used for the reaction. The method is preferably used for the production of dialkali salt solutions of dihydroxy diarylalkanes, such as for example, 4,4'-dihydroxy-2,2-diphenylpropane; 4,4'-dihydroxy-1,1-diphenylcyclohexane; 4,4'-dihydroxy-3,3',5,5'-tetramethyl-2,2-diphenylpropane; 4,4'-dihydroxy-3,3',5,5'-tetrachloro-2,2-diphenylpropane; 4,4'-dihydroxy-3,3',5,5'-tetrabromo-2,2-diphenylpropane. Sodium hydroxide is preferably used as the aqueous alkali hydrioxide solution.

Figures 1, 2:
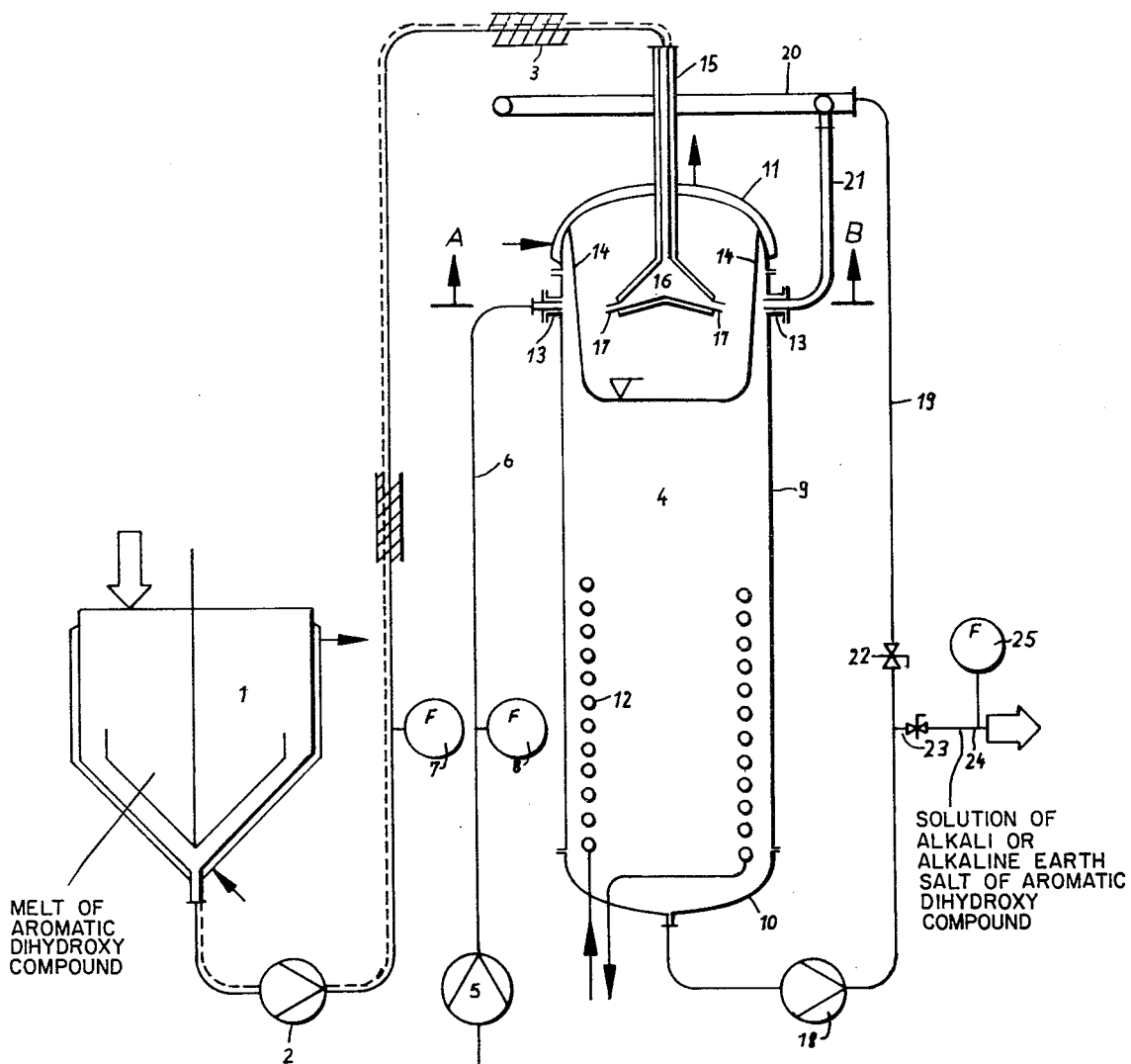
FIG. 1 is a diagrammatic illustration of an apparatus for use in carrying out the process according to the present invention.
FIG. 2 is a section on line A-B in FIG. 1.

The principle outlined above is described in more detail in the following with reference to one preferred embodiment of the method according to the invention. In this embodiment of the method according to the invention, which is illustrated in FIG. 1, an aromatic dihydroxy compound is melted in an appropriate vessel 1 and delivered by a pump 2, acting as a metering unit, through a heated pipe 3 into a reactor 4. The aqueous alkali solution, which may optionally contain special additives, is pumped through a pipe 6 into the reactor 4 by a delivery pump unit 5. The throughflows of the product streams introduced are controlled and recorded by means of throughflow meters 7 and 8.

The reactor 4 comprises a cylindrical container 9 and two covers 10 and 11. The cover 11 is heatable. A tubular coil 12, through which the heat of solution and reaction is dissipated, is installed in the lower part of the cylindrical container 9.

As shown in FIG. 2 (which is a section on the line A-B of FIG. 1), the upper part of the reactor comprises at least two, but advantageously several, tangential inlets 13 through which the reaction solution is introduced, so that a liquid film 14 is formed.

The melt of the aromatic dihydroxy compound is introduced from the vessel 1 through a heated pipe 15 into a similarly heated distributor chamber 16 and is sprayed through the nozzles 17, arranged around the periphery of the distributor chamber 16, onto the liquid film 14 where the dialkali salt solution is spontaneously formed.

The required development of the liquid film 14 is obtained by running in the aqueous alkali hydroxide solution through the pipe 6, and by introducing a component stream of the reaction solution from the reactor 4, which generally amounts to between 0.5 and 20 times the product stream from the pipe 6, through a pump 18 and a pipe 19. A ring pipe 20 distributes the stream of liquid from the pipe 19 to individual insertion tubes 21 which are introduced into the reactor through the inlets 13. The cross-sections of the insertion tubes 21 are of such dimensions that the liquid issuing from them produces the liquid film 14.

The dialkali salt solution is removed from the stream of liquid delivered by the pump 18 by means of regulators 22 and 23 and a flow meter 25 into a pipe 24 for further use.

By virtue of the method described above, it is possible, despite short reaction times, to produce from the melts of aromatic dihydroxy compounds the corresponding aqueous dialkali salt solutions both continuously and with a reproducible solids concentration. Instead of using an alkali hydroxide solution, it is also possible to use an alkaline earth hydroxide solution. In addition, it is possible to use this process for the production of solutions of dihydroxy compounds in organic solvents.

EXAMPLE

By introducing a bisphenol melt and a solution of sodium hdroxide in water, disodium bisphenolate solutions 1 to 7 are continuously produced in an apparatus as described with reference to the accompanying drawings which has a volume of 16 liters and a pump recirculation capacity of 900 liters per hour. The test parameters are shown in the following Table. For comparison, corresponding disodium bisphenolate solutions are prepared in batches in an 800 liter capacity vessel. The following procedure is applied for this purpose: a dilute sodium hydroxide is prepared by introducing water and 45% sodium hydroxide into a stirrer-equipped vessel. The dihydroxy compounds 1, 5, 6, 7 are introduced as solids, in the from of flakes, with vigorous stirring into these solutions over a period of 20 minutes in two portions. The required bisphenolate solutions are obtained after a total reaction time of 90 to 130 minutes.

The colour values of these batches and the necessary dissolution times are shown in the Table. For comparison, the volume-time yields of both processes are also quoted.

| Dihydroxy compound | Temp. [°C] | Throughput [kg/h] | Residence time [mins] | Sodium hydroxide conc. [% by weight] | Sodium hydroxide throughput [kg/h] | VTY [kg/l.h] | r[x) | Bisphenolate solution % solids | CV [Hz] | CV [Hz] | RT [min] | VTY [kg/h.l] |
|---|---|---|---|---|---|---|---|---|---|---|---|---|
| | | | | | | | | | | | Non-continuous batch for comparison | |
| 1. Bisphenol A | 165 | 50 | 1.9 | 3.90 | 450 | 3.13 | 1 | 10.0 | 5 | 15 | 90 | 0.067 |
| 2. | | 40 | 3.6 | 6.19 | 226.7 | 2.50 | 2 | 15.0 | 0–5 | | | |
| 3. | | 25 | 5.0 | 8.69 | **166.7 | 1.56 | 2 | 15.0 | 5 | | | |
| 4. | | 30 | 6.4 | 8.77 | 120 | 1.87 | 8 | 20.0 | 5 | 25 | 100 | 0.12 |
| 5. Tetramethyl bisphenol A | 175 | 25 | 7.7 | 7.04 | 100 | 1.56 | 2 | 20.0 | 10 | 35 | 130 | 0.092 |
| 6. Tetrachlor bisphenol A | 140 | 40 | 2.4 | 2.43 | 360 | 2.5 | 2 | 10.0 | 5–10 | 40 | 90 | 0.067 |
| 7. Bisphenol Z | 195 | 40 | 2.4 | 3.32 | 360 | 2.5 | 2 | 10.0 | 5–10 | 45 | 120 | 0.05 |

$^{x)}$r = ratio of pump-recirculated quantity (l) to quantity inroduced (l)
$^{xx)}$use of potassium hydroxide instead of sodium hydroxide
CV = colour value
RT = reaction time
VTY = volume-time yield An installation for producing a liquid film with a component stream of the reaction solution for carrying out the method according to the invention is distinguished by the fact that at least two insertion tubes 21 are connected to a ring pipe 20, leading into the reactor 4 through inlets 13 and forming an angle of less than 45° with the inner wall of the reactor.

The particular advantage of the installation according to the invention is that a uniform liquid film can be produced.

What we claim is:

1. A process for continuously producing solutions of dialkali or dialkaline earth metal salts of aromatic dihydroxy compounds, wherein an aromatic dihydroxy compound is sprayed in the form of a melt onto a turbulent liquid film containing the alkali or alkaline earth metal hydroxide in aqueous solution.

2. A process as claimed in claim 1, wherein the solution of an alkali or an alkaline earth metal hydroxide is an aqueous solution.

3. A process as claimed in claim 1, wherein the liquid film is produced in a reactor by tangentially introducing a stream of the solution of the alkali or alkaline earth metal hydroxide and the molten dihydroxy compound is sprayed through nozzle.

4. A process as claimed in claim 1, wherein the dihydroxy compound is bisphenol A, 1,1-bis-(4-hydroxyphenyl)-cyclohexane, tetramethyl bisphenol A, tetrachloro bisphenol A or tetrabromo bisphenol A and the solution of an alkali or an alkaline earth metal hydroxide is an aqueous solution of sodium hydroxide.

5. An apparatus for carrying out the process claimed in any preceding claim comprising at least two insertion tubes connected to a ring pipe, leading into a reactor through inlets and forming an angle of less than 45° with the wall of the reactor.

6. A process as claimed in claim 1, wherein said production is performed in a cylindrical reactor by introducing and contacting the aromatic dihydroxy compound and the metal hydroxide in an upper portion of the reactor for reaction thereof to form said solution of dialkali metal salt, said solution of dialkali metal salt is withdrawn from a bottom portion of the reactor, the turbulent liquid film is produced in said upper portion of the ractor by tangentially introducing a solution of the metal hydroxide into the upper portion of the reactor, and tangentially introducing a portion of the withdrawn solution of dialkali metal salt into the upper portion of the reactor, the amount of solution of dialkali metal salt so tangentially introduced being 0.5 to 20 times the amount of solution of the metal hydroxide so tangentially introduced.

7. A process as claimed in claim 6, wherein the solution of dialkali metal salt is cooled in the reactor.

8. A process as claimed in claim 6, wherein the average residence time of the solution of the dialkali metal salt in the reactor is between 0.5 and 20 minutes.

9. A process as claimed in claim 1, wherein the aromatic dihydroxy compound is dihydroxy diarylalkane.

10. A process as claimed in claim 1, wherein the aromatic dihydroxy compound is at least one of 4,4'-dihydroxy-2,2-diphenylpropane; 4,4'-dihydroxy-1,1-diphenylcyclohexane; 4,4'-dihydroxy-3,3',5,5'-tetramethyl-2,2-diphenylpropane; 4,4'-dihydroxy-3,3',5,5'-tetrachloro-2,2-diphenylpropane; 4,4'-dihydroxy-3,3',5,5'-tetrabromo-2,2-diphenylpropane.

11. A process as claimed in claim 9, wherein the metal salts are soluble in water.

12. A process as claimed in claim 1, wherein the average residence time is about 0.5 to 20 minutes.

* * * * *